United States Patent
Maayan et al.

(10) Patent No.: US 9,365,600 B2
(45) Date of Patent: Jun. 14, 2016

(54) POLYNUCLEAR METAL CLUSTERS, METHODS OF MAKING, AND METHODS OF USE THEREOF

(75) Inventors: Galia Maayan, Technion (IL); George Christou, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 127 days.

(21) Appl. No.: 14/009,828

(22) PCT Filed: Apr. 30, 2012

(86) PCT No.: PCT/US2012/035808
§ 371 (c)(1),
(2), (4) Date: Oct. 4, 2013

(87) PCT Pub. No.: WO2012/154436
PCT Pub. Date: Nov. 15, 2012

(65) Prior Publication Data
US 2014/0042035 A1  Feb. 13, 2014

(51) Int. Cl.
*C07F 13/00* (2006.01)
*B01J 29/06* (2006.01)
*C01B 3/04* (2006.01)
*C01B 13/02* (2006.01)
*B01J 31/22* (2006.01)
*C25B 1/04* (2006.01)

(52) U.S. Cl.
CPC ........... *C07F 13/005* (2013.01); *B01J 31/2226* (2013.01); *C01B 3/042* (2013.01); *C01B 13/0207* (2013.01); *C25B 1/04* (2013.01); *Y02E 60/364* (2013.01)

(58) Field of Classification Search
CPC ....... B01J 31/2226; C07F 13/005; C25B 1/04
USPC ................................ 205/628; 556/49; 502/70
See application file for complete search history.

(56) References Cited

U.S. PATENT DOCUMENTS

2003/0008770 A1   1/2003   Srinivas et al.
2010/0143811 A1   6/2010   Brimblecombe et al.

FOREIGN PATENT DOCUMENTS

WO   2010107919 A1   9/2010

OTHER PUBLICATIONS

Tasiopoulos et al., Polyhedron 26 (2007) 2183-2188.*
International Search Report dated Nov. 23, 2012.
Tasiopoulos, et al., "Synthetic Routes to a Family of Mn—Ce Heterometallic Clusters," Polyhedron, 2007, vol. 26, pp. 2183-2188.

* cited by examiner

*Primary Examiner* — Porfirio Nazario Gonzalez
*Assistant Examiner* — Kofi Adzamli
(74) *Attorney, Agent, or Firm* — Thomas Horstemeyer, LLP

(57) ABSTRACT

Embodiments of the present disclosure provide for polynuclear manganese cluster compounds, methods of making, methods of use, method of producing hydrogen and oxygen from water, and the like.

8 Claims, 10 Drawing Sheets

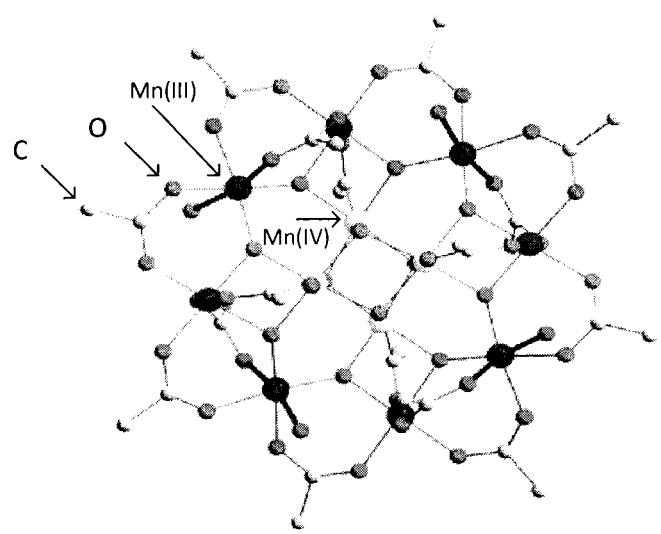
FIG. 1.1

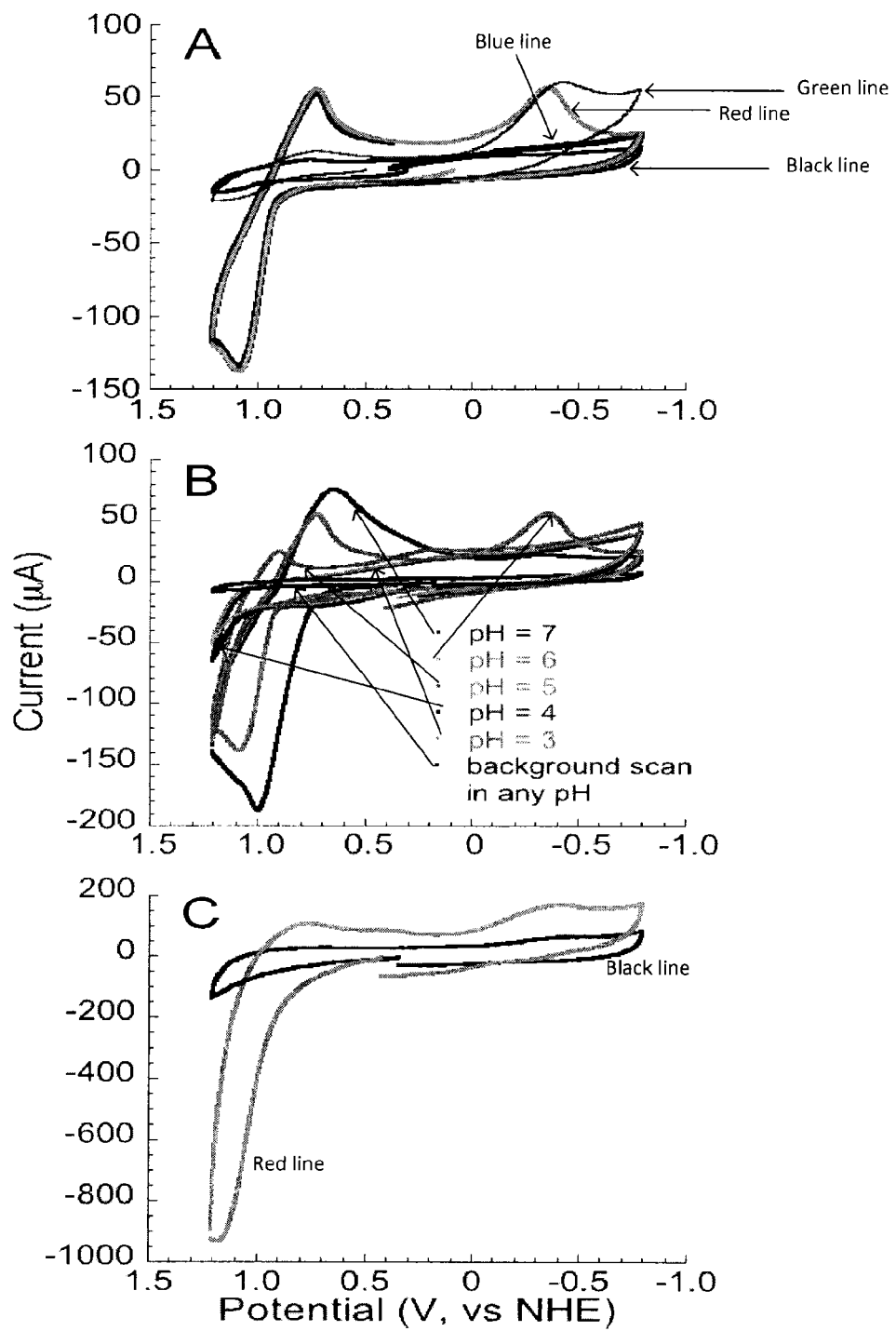
FIG. 1.2

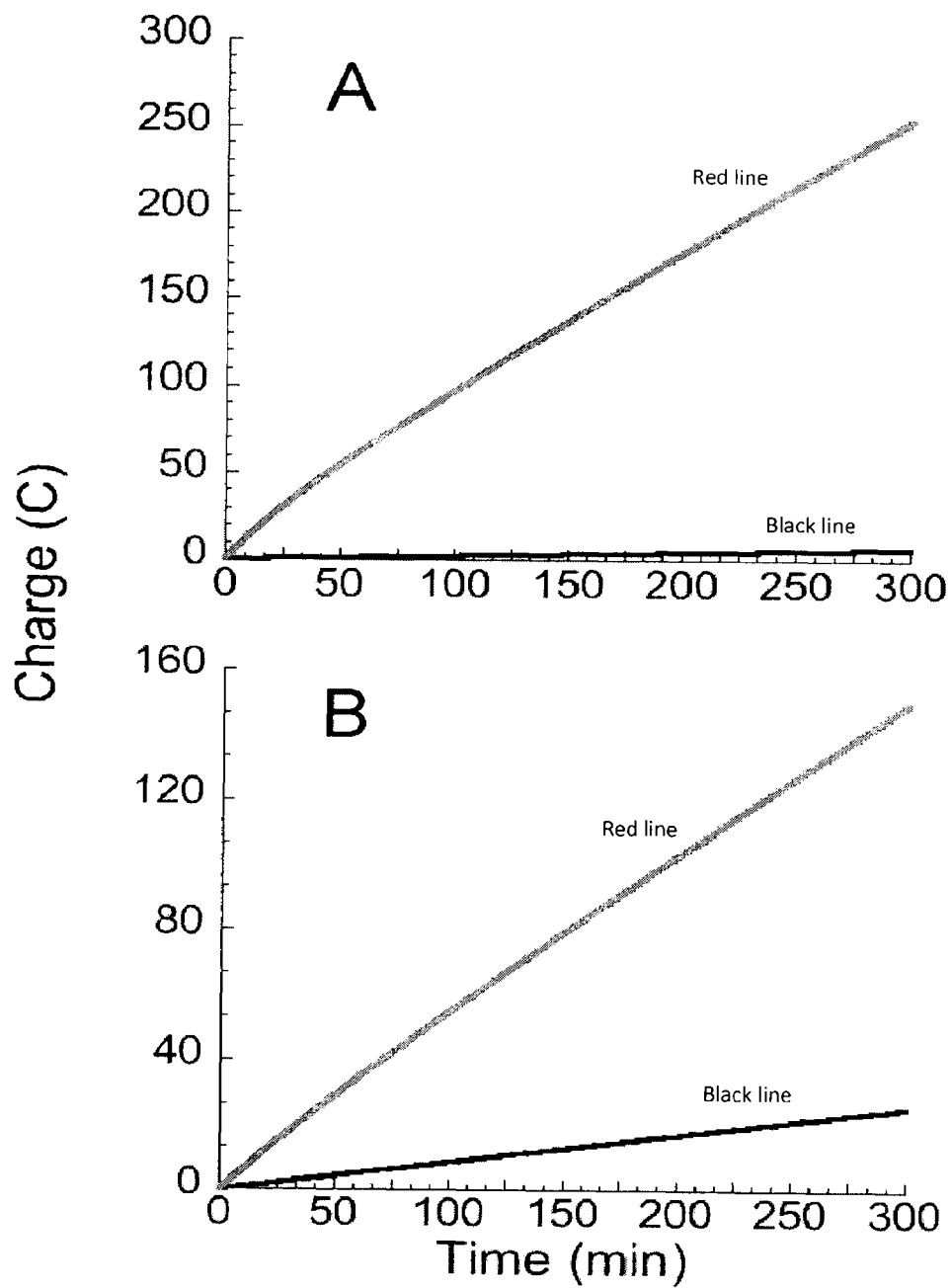
FIG. 1.3

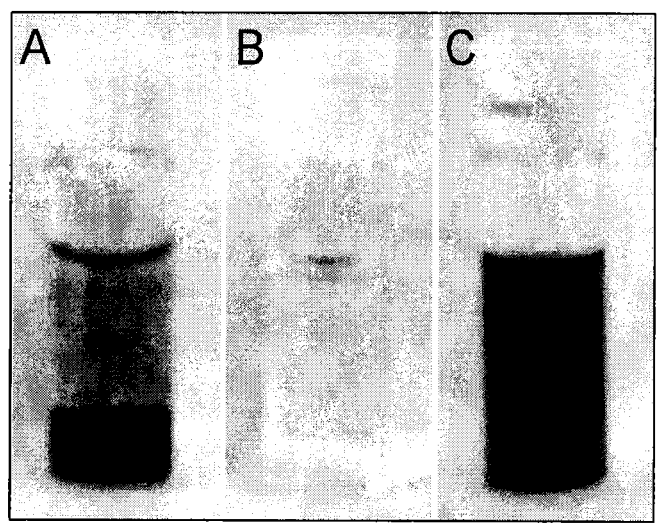
FIG. 1.4

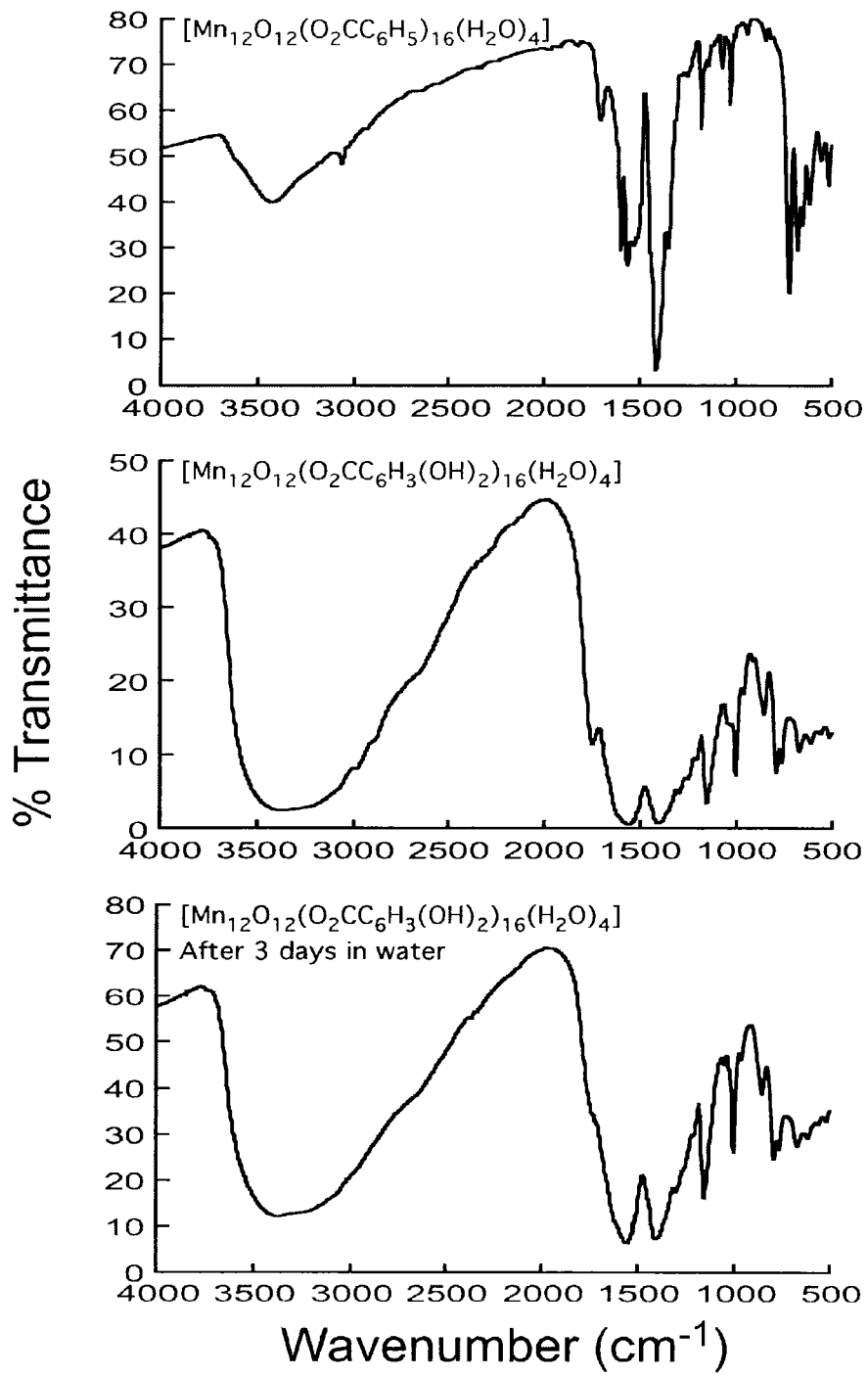
FIG. 1.5

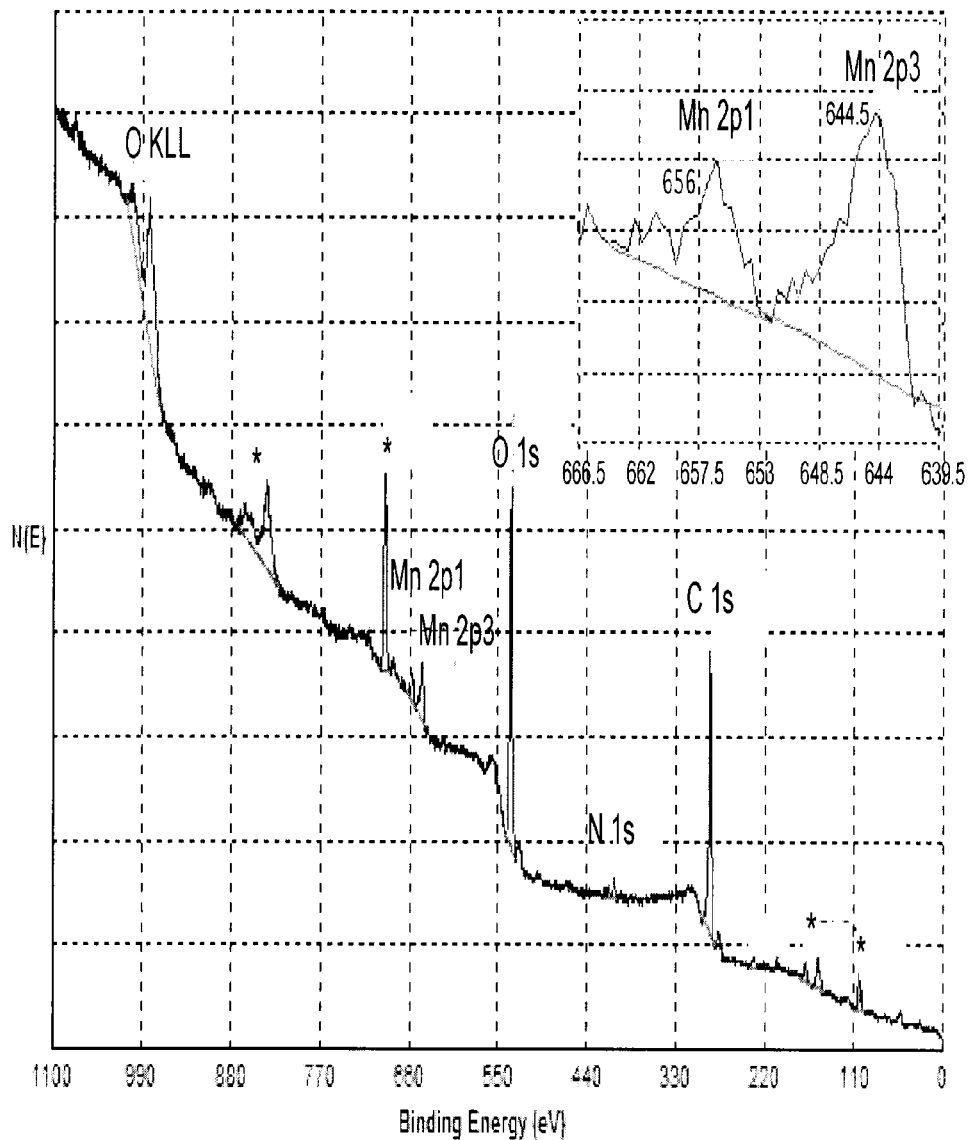
FIG. 1.6

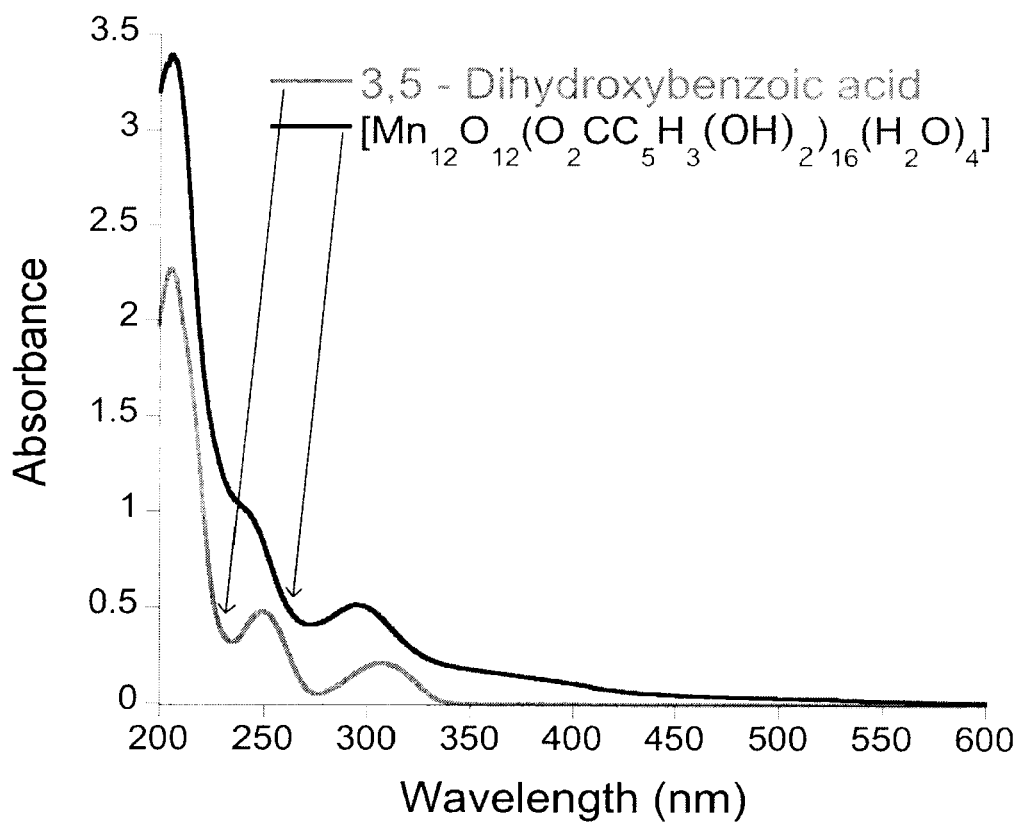
FIG. 1.7

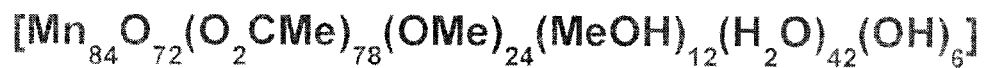
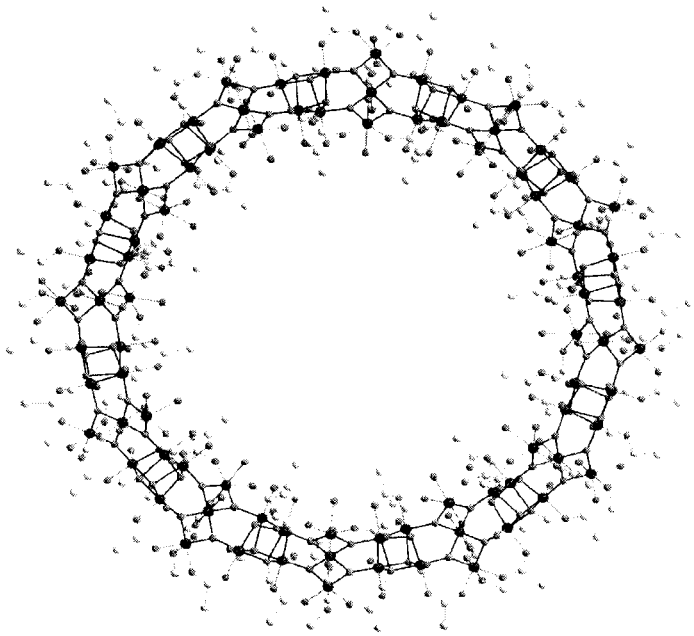
FIG. 2.1
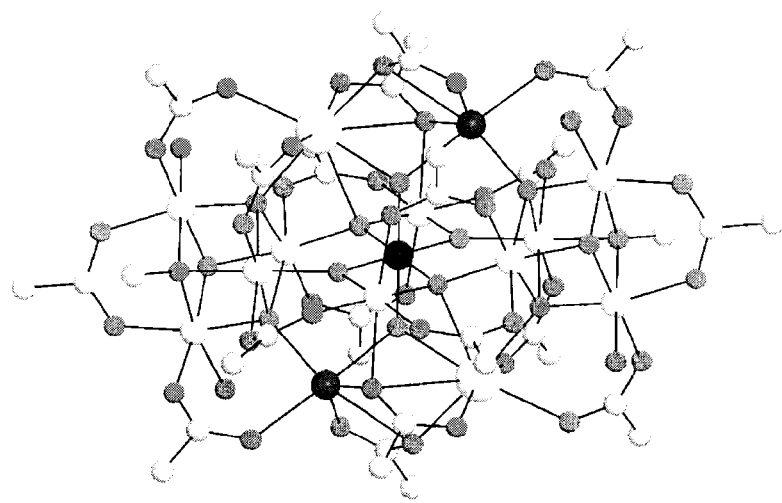
FIG. 2.2

$[Mn_{14}SrO_{11}(OMe)_3(O_2CPh)_{18}(MeCN)_2]$
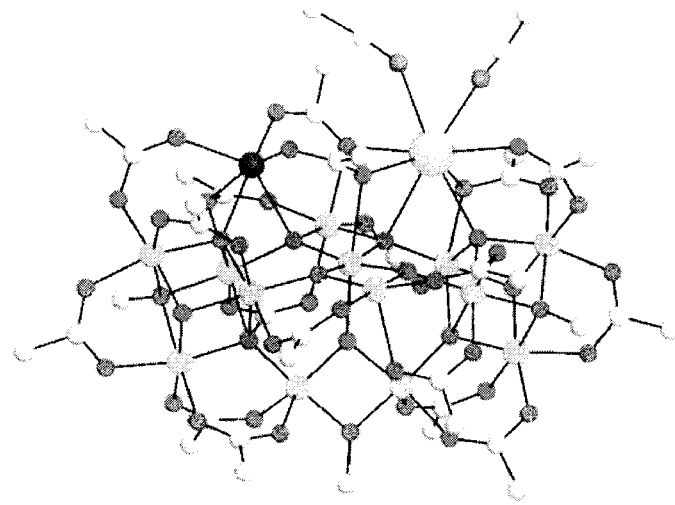
FIG. 2.3
$[Mn_3Ca_2O_4(O_2CR)_8(RCO_2H)_4]$
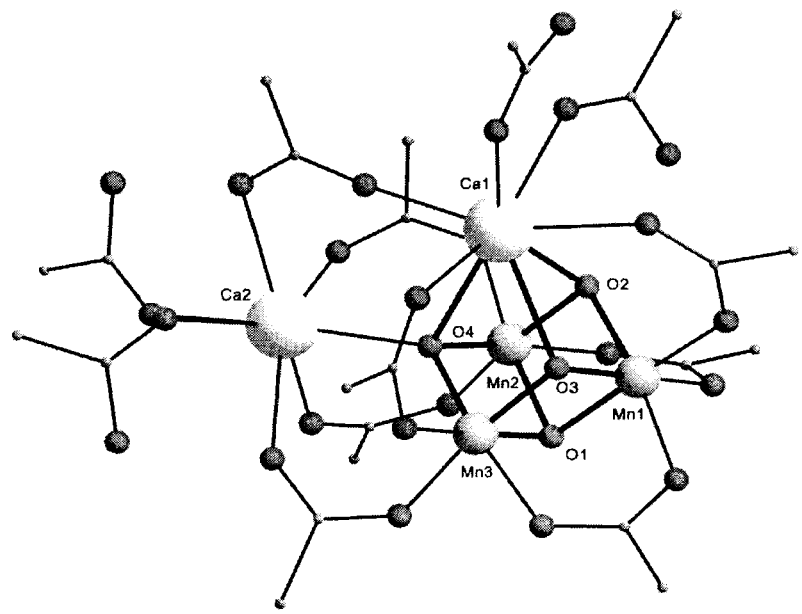
FIG. 2.4

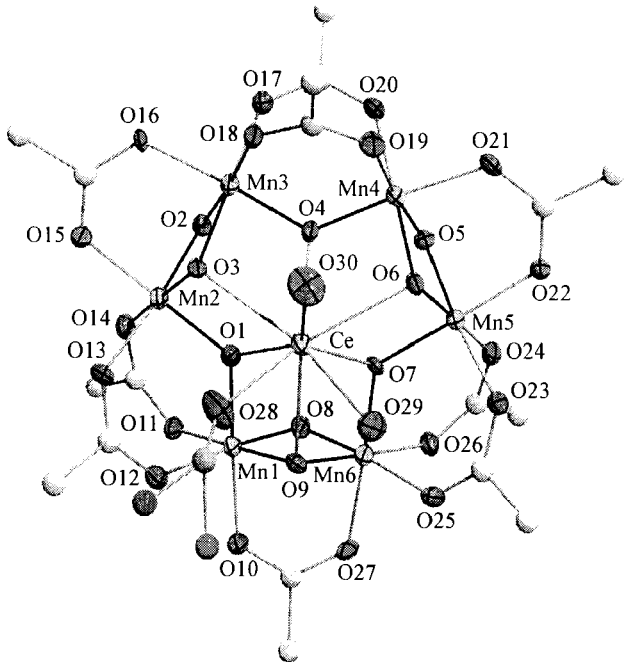
FIG. 2.5
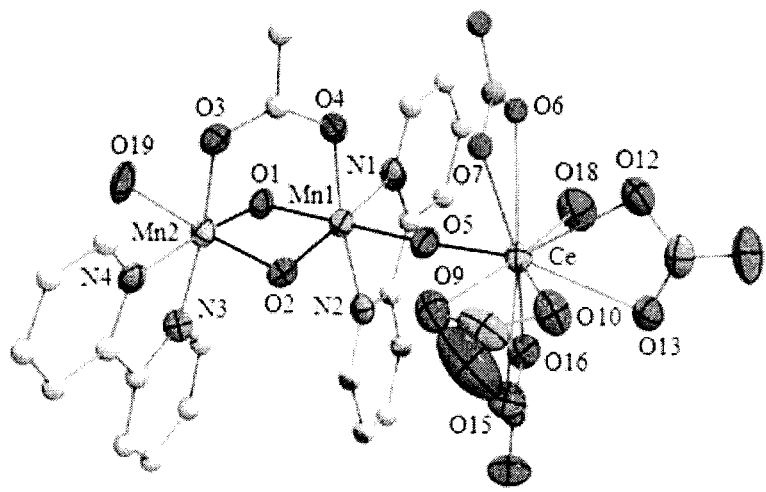
FIG. 2.6

POLYNUCLEAR METAL CLUSTERS, METHODS OF MAKING, AND METHODS OF USE THEREOF

STATEMENT REGARDING FEDERALLY SPONSORED RESEARCH OR DEVELOPMENT

This invention(s) was made with government support under Grant No.: CHE-0910472 awarded by the National Science Foundation. The government has certain rights in the invention(s).

CROSS-REFERENCE TO RELATED APPLICATION(S)

This application is the 35 U.S.C. §371 national stage of PCT application PCT/US2012/35808, filed Apr. 30, 2012, which claims priority to and the benefit of U.S. Provisional Application Ser. No. 61/483,212, filed May 6, 2011, both of which are hereby incorporated by reference herein in their entirety.

BACKGROUND

In natural photosynthesis, the catalytic splitting of water into oxygen and hydrogen utilizes sunlight energy and a high oxidation state manganese cluster. Few synthetic high-valent manganese complexes have been applied to date as water oxidation catalysts in homogeneous and heterogeneous systems. The use of electrochemical energy for homogeneous water oxidation catalyzed by a manganese cluster, however, has not been demonstrated.

SUMMARY

Embodiments of the present disclosure provide for polynuclear manganese cluster compounds, methods of making, methods of use, method of producing hydrogen and oxygen from water, and the like.

An embodiment of the present disclosure includes a composition that includes a polynuclear manganese cluster compound having oxygen-containing groups, wherein each oxygen-containing group is independently selected from the group consisting of: a carboxylate group, an alcohol group, an alkoxide group, an ether group, and a combination thereof.

An embodiment of the present disclosure includes a method of generating hydrogen and oxygen from water that includes: dissolving a composition in an aqueous solution; and applying a voltage applied between electrodes disposed in the aqueous solution, and generating hydrogen and oxygen, wherein the composition is a polynuclear manganese cluster compound having oxygen-containing groups, wherein each oxygen-containing group is independently selected from the group consisting of: a carboxylate group, alcohol group, alkoxide group, ether group, and a combination thereof.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1.1 illustrates an X-ray structure of $[Mn_{12}O_{12}(O_2CMe)_{16}(H_2O)_4]$. Mn(IV) ions are green; Mn(III), blue; O atoms, red; and C, gray. Hydrogen atoms are omitted for clarity.

FIG. 1.2 illustrates cyclic voltammograms at a scan rate of 100 mVs$^{-1}$ in (A) 0.1M acetate buffer at pH 6.0 with no Mn cluster or oxygen present (black line), with only oxygen present (green line, 10 atmospheres of oxygen pressure were bubbled into the solution for 5 minutes) and with 0.5 mM Mn cluster 1 present (blue and red lines, 10 atmospheres of nitrogen were bubbled into the solution for 5 minutes prior to the measurements); (B) 0.1M sodium acetate electrolyte and (C) seawater. The potential was measured against a Ag/AgCl reference and converted to NHE potentials by using E(NHE)=E(Ag/AgCl)+0.21 V.

FIG. 1.3 illustrates bulk electrolysis. Electrolysis data for a 14-18 mL solution containing 5.6 μmole of 1 in 0.1M pH 7 acetate buffer (A) and seawater (B) showing charge build-up versus time (red line), and data for the buffer solution alone showing charge build-up versus time (black line) with the cell operating at a potential of 1.21V versus NHE.

FIG. 1.4 illustrates vials containing water and (A) $[Mn_{12}O_{12}(O_2CMe)_{16}(H_2O)_4]$ ($Mn_{12}$ acetate), which dissolved to give a brown solution that rapidly hydrolyzed to a flocculent brown precipitate; (B) $[Mn_{12}O_{12}(O_2CC_6H_5)_{16}(H_2O)_4]$ ($Mn_{12}$ benzoate), which is insoluble and the powder is floating on the surface; and (C) compound 1, which has dissolved to give a persisting brown solution.

FIG. 1.5 illustrates FT-IR spectra of (A) $Mn_{12}$ benzoate, $[Mn_{12}O_{12}(O_2CC_6H_5)_{16}(H_2O)_4]$, (B) compound 1, and (C) compound 1 after dissolution in water for three days, and re-isolation as a solid. The spectra were measured in the solid state as potassium bromide pellets.

FIG. 1.6 illustrates X-ray Photoelectron Spectroscopy (XPS) spectrum of 1. Samples were excited with an Al X-ray source; pass energy of 89.45 eV and work function of 5.15 eV.

FIG. 1.7 illustrates UV/vis spectra of 3,5-dihydroxybenzoic acid (red curve) and 1 (blue curve) in water.

FIGS. 2.1 to 2.6 illustrate embodiments of the present disclosure.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. Terms defined in references that are incorporated by reference do not alter definitions of terms defined in the present disclosure or should such terms be used to define terms in the present disclosure they should only be used in a manner that is inconsistent with the present disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, inorganic chemistry, material science, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

The term "water-soluble" refers to a polynuclear manganese cluster compound that can be dissolved (e.g., about 80% or more, about 90% or more, about 95% or more, about 99% or more, or about 99.9% or more) in water, and can be completely dissolved if sufficient water is used.

The term "water-stable" refers to a polynuclear manganese cluster compound that does not undergo any significant (e.g., less than about 10%, less than about 5%, less than about 3%, less than about 1%, or less than about 0.1%, decomposition) decomposition when dissolved in water.

As used herein, "alkyl" or "alkyl group" refers to a saturated aliphatic hydrocarbon which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "substituted" refers to any one or more hydrogens on the designated atom that can be replaced with a selection from the indicated group, provided that the designated atom's normal valence is not exceeded, and that the substitution results in a stable compound.

The term "substituted," as in "substituted alkyl", "substituted aryl," "substituted heteroaryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

Discussion

Embodiments of the present disclosure provide for polynuclear manganese cluster compounds, methods of making, methods of use, method of producing hydrogen and oxygen from water, and the like.

Embodiments of the polynuclear manganese cluster compound are advantageous in that they may be water-soluble and water-stable. These characteristics may allow the polynuclear manganese cluster compound to mimic the water oxidizing complex (WOC) in plants and bacteria by carrying out catalytic homogeneous water splitting for the efficient generation of molecular hydrogen as an alternative source of fuel. Embodiments of the present disclosure have shown that they can carry out homogeneous electrocatalytic splitting of water, including seawater in low potential and relatively high turn-over-number (TON). Additional details are provided in Example 1.

Embodiments of the polynuclear manganese cluster compound are advantageous in that they can overcome one or more of the current challenges in generating homogeneous water oxidation catalysts by providing ones that are (i) prepared from inexpensive and readily available materials as well as abundant metal ions; (ii) highly soluble and stable in water; (iii) employ photochemical and/or electrochemical energy in low potential or chemical oxidants, which do not contain oxygen atoms; (iv) active in natural water including seawater and (v) perform in relatively low concentration and with relatively high TON.

Embodiments of the present disclosure include polynuclear manganese cluster compounds having oxygen-containing groups, which appear to improve water solubility of the polynuclear manganese cluster compounds. The polynuclear manganese cluster compound can include 2, 3, 4, 6, 8, 12, 13, and 14, to 84 manganese atoms, where the number of oxygen-containing groups can vary depending upon the number of manganese atoms. The polynuclear manganese cluster compound can also include water groups ($H_2O$), and the number of water groups can vary depending upon the structure of a particular compound and its method of preparation. Although not intending to be bound by theory, the surrounding ligands provide water solubility and stability, while the high-oxidation state cores act as catalytic centers, providing the electrochemical evolution of oxygen and hydrogen from water. In general, the cluster compounds contain up to two water solubility groups per Mn.

In an embodiment, the oxygen-containing groups (ligands) can include, but are not limited to, a carboxylate group, an alcohol and alkoxide group, an ether group, or a combination thereof, where each R group can be individually selected (e.g., two or more different types of oxygen-containing groups can be included in a single polynuclear manganese cluster compound). In an embodiment, the carboxylate group can be selected from $O_2CC_5H_3(OH)_q$, where q is 2 to 5, $O_2CC_3H_6O$ and $O_2CC_2H_5O$. In an embodiment, the alcohol group can include $X(X')(X'')$—C—OH, wherein X, X', and X" are independently selected from an alkyl group (substituted or unsubstituted), an aryl group (substituted or unsubstituted), and a heteroaryl group (substituted or unsubstituted). In an embodiment, the alkoxide group can include $X(X')(X'')$—C—O$^-$, wherein X, X', and X" are independently selected from an alkyl group (substituted or unsubstituted), an aryl group (substituted or unsubstituted), and a heteroaryl group (substituted or unsubstituted). In an embodiment, the ether group can include $(X-O-X')_n$, wherein n can be greater than 1 or 1 to 1000, wherein X and X' are independently selected from an alkyl group (substituted or unsubstituted), an aryl group (substituted or unsubstituted), and a heteroaryl group (substituted or unsubstituted). In an embodiment, the ether group can be oligomeric or polymeric.

In particular, embodiments of the present disclosure include compounds having the general formula $Mn_xM_yR_z$. R is an oxygen containing ligand such as those described herein, M is a metal such as Ca, Sr, or Ce, x can be 2 to 84, y can be 0 to 10, 0 to 6, or 0 to 2, and z can be 2 to 100, 2 to 60, or 2 to 24.

In an embodiment, the polynuclear manganese cluster compound can be represented by one of the following formulas: $Mn_{12}O_{12}(O_2CR)_{16}(H_2O)_4$, $Mn_{84}O_{72}(R)_{24}(H_2O)_{42}$, $Mn_{13}Ca_2O_{10}(R)_{18}(H_2O)_4$, $Mn_{14}SrO_{11}(R)_{18}(H_2O)_4$, $Mn_3Ca_2O_4(R)_8(H_2O)_a$, $Mn_6CeO_9(R)_9(H_2O)_a$, and $Mn_2CeO_3(R)_2(H_2O)_a$, where each R is independently selected from the oxygen-containing group noted herein and a is varied depending on the structure of the cluster but can be 0 to 6. Exemplar structures of compounds that can be converted into these compounds are described in Example 2

Embodiments of the present disclosure include methods of generating hydrogen and oxygen from water, even saline or salt water. In short, a method includes dissolving a polynuclear manganese cluster compound in an aqueous solution. In an embodiment, the polynuclear manganese cluster compound is soluble in the aqueous solution. A voltage can be applied between electrodes dipping in the aqueous solution, and the polynuclear manganese cluster compound catalyzes the reaction of the water molecules to produce hydrogen and oxygen. The voltage potential can be about 0.9V to 1.4V. Additional details are provided in the Examples.

EXAMPLE

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

In natural photosynthesis, the catalytic splitting of water into oxygen and hydrogen utilizes sunlight energy and a high oxidation state manganese cluster. Few synthetic high-valent manganese complexes have been applied to date as water oxidation catalysts in homogeneous and heterogeneous systems. The use of electrochemical energy for homogeneous water oxidation catalyzed by a manganese cluster, however, has not been demonstrated. Herein we present the synthesis and characterization of a unique polynuclear Mn cluster, $[Mn_{12}O_{12}(O_2CC_5H_3(OH)_2)_{16}(H_2O)_4]$, which is highly soluble and stable in water as indicated by spectroscopic studies. Electrochemical investigations in acetate buffer solutions revealed pH dependent catalytic currents at an oxidation potential as low as 1.0V vs the NHE (NHE is the Normal Hydrogen Electrode). $O_2$ evolution was clearly detected by a typical reduction peak observed in cyclic voltammograms. Controlled potential electrolysis indicates that this catalyst not only performs with high turnover number in low potential, but also functions in seawater.

The catalytic splitting of water into hydrogen and oxygen is a bio-inspired challenge for chemists seeking to find "green" alternatives for fuel. In nature, specifically in green plants and cyanobacteria, the water oxidizing complex (WOC) near photosystem II (PS II) is able to catalyze the oxidation of $H_2O$ exploiting absorbed sunlight followed by electron transfer.[1,2] This four-electron process (Scheme 1) involves various oxidation levels of the WOC (the so-called Sn states, n=0 to 4),[1, 2] and is the source of essentially all the $O_2$ on this planet. The WOC has been studied extensively, and it is known to involve a $CaMn_4O_4$ cluster at its core.[3, 4] Consequently, a variety of nonbiological inorganic mimics of the WOC have been developed. A few manganese clusters,[5-9] as well as cobalt,[10-12] ruthenium[13-14] and iridium[15] complexes have been applied as water oxidation catalysts in both heterogeneous and homogeneous systems.[16] Among these, the use of high oxidation manganese complexes is of particular interest due to their biological relevance and structure-function studies of such synthetic clusters lead to significant contributions to the field of water oxidation catalysis.[17-20] Homogeneous water oxidation manganese catalysts, however, typically utilize chemical oxidants, such as peroxides, oxone and per-chlorate, which might participate in the water oxidation reaction itself, resulting in uncertainty regarding the source of the evolved $O_2$.

Scheme 1.

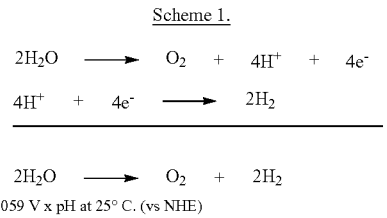

$E = 1.23\text{ V} - 0.059\text{ V} \times \text{pH at } 25°\text{ C. (vs NHE)}$ In order to avoid this ambiguity, the one-electron Ce(IV) oxidant was employed instead of the oxygen donor agents in a few homogeneous[9, 21] and heterogeneous[10, 11] manganese-based catalytic systems, however, with very low (<2 h$^{-1}$) or with no turnover number. An alternative approach, which is also a great a challenge, is to follow nature's way and seek for catalysts employing photochemical or electrochemical energy at low over potentials. Examples of heterogeneous water oxidation photocatalysis by manganese dimmer/[Ru(bpy)$_3$]$^{2+}$/mica[22] and manganese-cubane/Nafion[8, 23] catalysts have been recently reported, with turnovers of 3.4 in 17 hr and 1000 in 65 hr, respectively. Notably, the manganese-cubane activity is limited to heterogeneous systems because of is low solubility in water. Therefore, water-soluble manganese clusters that can efficiently utilize sunlight or low potential electrochemical energy for the catalytic homogeneous production of oxygen and hydrogen from water have yet to be discovered.

The class of polynuclear manganese clusters [Mn$_{12}$O$_{12}$(O$_2$CR)$_{16}$(H$_2$O)$_4$] (Mn$_{12}$; R=Me, Et, Ph, etc.) have been well investigated by our group and others.[24] These clusters have several properties, which make them potential catalysts for water oxidation: (i) they are prepared by convenient, high-yield procedures including carboxylate substitution; (ii) they contain high oxidation state metal ions (8Mn(III), 4Mn(IV)); (iii) they are stable towards oxidation processes and (iv) they display multiple one-electron reversible reductions at high potentials. However, these complexes are either not soluble or not stable in water, or both and have not been employed as water oxidation catalysts.

In this example we report a homogeneous catalyst, [Mn$_{12}$O$_{12}$(O$_2$CC$_5$H$_3$(OH)$_2$)$_{16}$(H$_2$O)$_4$] (1), which is highly soluble and stable in water. It is easily prepared from readily available manganese salt, manganese oxide, and 3,5-dihydroxybenzoic acid. In addition, its facile two-steps synthesis (Scheme 2) employs benign solvents such as water, acetic acid and acetonitrile, and is performed at 25° C. In the first step, [Mn$_{12}$O$_{12}$(O$_2$CCH$_3$)$_{16}$(H$_2$O)$_4$] (Mn$_{12}$ acetate, FIG. 1.1) is prepared by mixing water/acetic acid solutions of KMnO$_4$ and Mn(CH$_3$COO)$_2$ followed by slow evaporation at room temperature. The second step involves a carboxylate substitution reaction between the methyl acetate ligands (pKa of acetic acid=4.76 at 25° C.) and the dihydroxybenzoate ligands (pKa of 3,5-dihydroxybenzoic acid=4.04 at 25° C.). The brown product 1 is spontaneously precipitated from an acetonitrile solution, collected by filtration, washed with acetonitrile to remove residues of un-reacted compounds and dried.

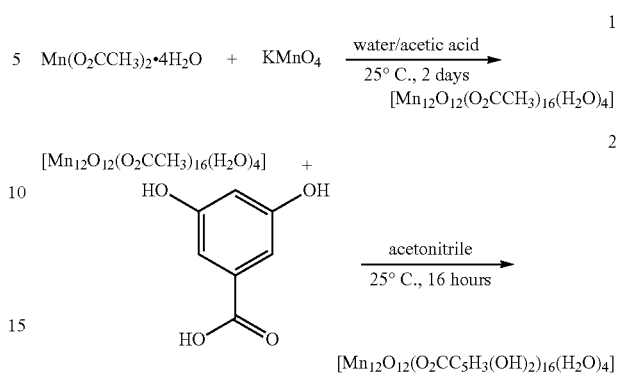

Scheme 2.

As mentioned above, Mn$_{12}$ acetate is not stable in water. As soon as water is added to solid Mn$_{12}$ acetate and the cluster starts to dissolve, a rapid hydrolysis occurs and brown aggregates of Mn oxides precipitate out from the solution (FIG. 1.4A). Substitution of the methyl acetate ligands by the more bulky and hydrophobic benzoate ligands is expected to create a hydrophobic shell around the Mn$_{12}$O$_{12}$ core and protect it from decomposition in water. However, even though the substitution product, [Mn$_{12}$O$_{12}$(O$_2$CC$_5$H$_5$)$_{16}$(H$_2$O)$_4$] (Mn$_{12}$ benzoate), does not undergo hydrolysis in water, it is also not soluble in water (FIG. 1.4B). Cluster 1 was therefore designed to have numerous hydroxyl groups surrounding the hydrophobic shell, anticipating that these hydrophilic units will enable water solubility while keeping the core intact in the water solution. Indeed, upon addition of water to solid 1, the cluster dissolved completely and stays stable (no precipitation occurs) for months (FIG. 1.4C). Cluster 1, which is only soluble in water and in dimethylsulfoxide, was characterized by elemental analysis and a variety of spectroscopic methods including FT-IR, XPS, and UV. The spectra obtained were compared with the corresponding characteristic spectra of the known clusters Mn$_{12}$ benzoate and Mn$_{12}$ acetate.

A typical IR spectrum of any [Mn$_{12}$O$_{12}$(O$_2$CR)$_{16}$(H$_2$O)$_4$] cluster includes a broad absorbance band at v=3300 cm$^{-1}$ assigned to the O—H stretching, which is characteristic of hydroxyl group of H$_2$O hydrated, a group of bands at v=1800-1000 cm$^{-1}$ associated with the different carboxylate stretching and an additional group of bands in the vicinity of 790-430 cm$^{-1}$, which corresponds to the diverse range of Mn oxide stretching (FIG. 1.5A). The IR spectra of 1 is very similar to that of Mn$_{12}$ benzoate, with two differences: (1) the broad absorbance band at v=3300 cm$^{-1}$ is much stronger, due to the additional O—H stretching, which corresponds to the hydroxyl groups on the benzoate ligands, and (2) a new absorbance band at v=856 cm$^{-1}$ associated with the aromatic C—OH stretching is present (FIG. 1.5B). In order to verify that the structure of 1 is stable in water and does not get decomposed or modified, it was dissolve in water and after three days the solution was freeze-dried. The IR spectrum of the dried compound (FIG. 1.5C) is identical to the one depicted in FIG. 1.5B. These IR spectra suggest that 1 has the same structure as Mn$_{12}$ benzoate, or of any other member in the [Mn$_{12}$O$_{12}$(O$_2$CR)$_{16}$(H$_2$O)$_4$] class of clusters. The composition of 1 was confirmed by elemental analysis; the values found, 38.47% C, 3.35% H and 0.90% N, were consistent with the calculated values for [Mn$_{12}$O$_{12}$(O$_2$CC$_5$H$_3$(OH)$_2$)$_{16}$(H$_2$O)$_4$]·2CH$_3$CN·10H$_2$O (38.33% C, 3.16% H and 0.77% N). The structure of 1 was further verified by XPS analysis.

The analyzed monolayer was dried from a water solution, and the spectrum obtained was found to be similar to the one of $Mn_{12}$ acetate, having two typical Mn—O peaks[25] (FIG. 1.6). Additionally, in order to establish the presence of 3,5-dihydroxybenzoate ligand in cluster 1, UV-Vis measurements were performed (FIG. 1.7). Cluster 1 exhibits two absorption bands, near $\lambda=240$ nm and 300 nm, which are 10 nm shifted relative to the free 3,5-dihydroxybenzoic acid ($\lambda=250$ nm and 310 nm), with the band near $\lambda=240$ being much less resolved, as expected in an environment of metal ions. Overall, these results confirm that compound 1 is a new member of the $Mn_{12}$ carboxylate class of clusters.

The electrochemical behavior of 1 was initially evaluated in acetate buffer at pH 6.0. Acetate buffer was employed as the electrolyte solution of choice because it has been previously shown that high oxidation manganese dimmers are capable of catalyzing oxygen evolution from water using strong oxidants such as oxone in acetate buffer solutions.[26, 27] As depicted in FIG. 1.2A, the cyclic voltammogram of 1 in acetate buffer at pH 6 is quasi reversible—when the current was applied in the positive direction one anodic peak and two cathodic peaks were observed, (FIG. 1.2A, red line). The positive anodic peak corresponds to the consequent oxidation of an outer Mn(III) ion by one electron to Mn(IV) followed by the increasing baseline corresponding to catalytic water oxidation at a peak potential (E) of 1.08 V versus the normal hydrogen electrode (NHE). The positive cathodic peak at $E=0.75$ V is assigned to the reduction of the outer Mn(IV) ion back to the Mn(III) starting state. The negative cathodic peak at $E=-0.4$ V may be assigned to the reduction of oxygen, which presumably is being evolved in this electrocatalytic water oxidation process. The reduction potential of molecular oxygen in these reaction conditions was verified by a cyclic voltammogram experiment done in an acetate buffer solution that contained molecular oxygen in the absence of 1 (FIG. 1.3A, green line). Assuming that this reduction behavior is assigned to molecular oxygen, which is evolved during the water oxidation process, the negative cathodic peak at $E=-0.4$ V is not expected to appear in case the current will flow in the opposite direction, when the oxidation event takes place after the reduction event. Indeed, when the current was applied in the negative direction, this cathodic peak is not observed because the catalytic oxidation occurs later, in a higher potential (FIG. 1.2A, blue line). This result provides a significant evidence for the evolution of molecular oxygen in this catalytic oxidation reaction.

During the water oxidation process (Scheme 1), there are four protons being released for each oxygen molecule that is formed. Therefore, the observation that 1 can oxidize water to generate $O_2$ at slightly acidic pH was unexpected and led us to test its electrochemical behavior in various pH values. As 1 rapidly decomposes at pH>7, cyclic valtommograms were measured in acetate buffer solutions with pH ranging from 7 to 3 (FIG. 1.2B). Significant catalytic currents were only observed in pH=5-7 in E values, which are pH dependent. The most intense catalytic peak was obtained at pH=7, with the lowest E value of only 1.0 V vs. the NHE. The increase in potential with the decrease in pH is consistent with this oxidation process, which is kinetically not favored in acidic solution. Cyclic voltammogram experiment was also performed in seawater with no added electrolyte (FIG. 1.2C) and a catalytic oxidation wave was observed at a potential of 1.21V vs. the NHE.

Controlled potential electrolysis (CPE) experiments were carried out in a double-compartment cell and applied potential of 1.0V vs. Ag/AgCl to assess the efficacy of 1. As shown in FIG. 1.3, 1 is an effective catalyst for the electrochemical oxidation of natural water (FIG. 3A) with charge accumulation of 254.3 C in 5 hours, whereas a control experiment run under identical conditions, but without the catalyst, showed a charge accumulation of only 6.9 C. The charge collected over this period, after subtracting the contribution from the blank solution, resulted in a turnover number of 114.2 moles of $O_2$ per mole of catalyst with a turnover frequency (TOF) of 22.8 moles of $O_2$ per mole of catalyst per hour. To the best of our knowledge, not only this is the first example of efficient, low potential, electrochemical water oxidation by a manganese cluster, but also these values are higher than any other reported manganese catalysts for water oxidation reaction. Moreover, this catalyst operates in seawater at the potential of 1.21V with the accumulation of 149.6 C in 5 hours, which after subtracting the contribution from the blank solution, corresponds to 57.2 moles of $O_2$ per mole of catalyst with a TOF of 11.4 moles of $O_2$ per mole of catalyst per hour. One explanation for the high activity at pH 7 as well as in seawater might be related to the phenol type hydroxyl groups on the benzoate ligands in cluster 1, having pKa values of 10.3 and 9.0,[28] which might act as additional proton acceptors in this reaction, enabling the high TON of oxygen evolution.

The discovery of a water-soluble manganese catalyst for the electrochemical oxidation of water to form oxygen and hydrogen in low potential and high turnover frequency is a crucial step toward the designing of efficient biomimetic catalysts that are highly active and robust in aqueous media. Ongoing efforts are focused on applying various water-soluble carboxylate ligands to $Mn_{12}$ as well as to smaller high oxidation manganese and calcium-manganese to further facilitate charge- and light-driven catalytic processes relevant to sustainable energy.

References, each of which is incorporated herein by reference:

1 H. Dau, I. Zaharieva, *Acc. Chem. Res.* 42, 1861-1870 (2009).
2 J. Barber, *Philos. Trans. R. Soc. London Ser. A* 365, 1007 (2007).
3 C. W. Hoganson, G. T. Babcock, *Science* 277, 1953 (1997).
4 P. E. M. Siegbahn, *Acc. Chem. Res.* 42, 1871 (2009).
5 K. N. Ferreira, T. M. Iverson, K. Maghlaoui, J. Barber, S. Iwata, *Science* 303, 1831 (2004).
6 J. Yano et al., *Science* 314, 821 (2006).
7 J. Limburg, J. S. Vrettos, L. M. Liable-Sands, A. L. Rheingold, R. H. Crabtree, G. W. Brudvig, *Science* 283, 1524 (1999).
8 R. Tagore, R. H. Crabtree, G. W. Brudvig, *Inorg. Chem.* 47, 1815 (2008)
9 G. C Dismukes, R. Brimblecombe, G. A. N. Felton, R. S. Pryadun, J. E. Sheats, L. Spiccia, G. F. Swiegers, *Acc. Chem. Res.* 42, 1935 (2009).
10 A. K. Poulsen, A. Rompel, C. J. McKenzie, *Angew. Chem. Int. Ed.* 44, 6916 (2005).
11 M. M. Najafpour, T. Ehrenberg, M. Wiechen, P. Kurz, *Angew. Chem. Int. Ed.* 49, 2233 (2010).
12 M. W. Kanan, D. G. Nocera, *Science* 321, 1072 (2008).
13 F. Jiao, H. Frei, *Angew. Chem. Int. Ed.* 48, 1841 (2009).
14 Q. Yin et al., *Science* 328, 342 (2010).
15 Y. V. Geletii et al., *J. Am. Chem. Soc.* 131, 7522 (2009).
16 T. J. Meyer et al., *Acc. Chem. Res.*, 42, 1954 (2009)
17 W. J. Youngblood et al., *J. Am. Chem. Soc.* 131, 926 (2009).
18 X. Sala, I. Romero, M. Rodriguez, L. Escriche, A. Llobet, *Angew. Chem. Int. Ed.* 48, 2842 (2009).
19 M. Yagi, M. Kaneko, *Chem. Rev.* 101, 21 (2001).
20 R. Manchanda, G. W. Brudvig, R. H. Crabtree, *Coord. Chem. Rev.* 144, 1 (1995).
21 W. Ruettinger, G. C. Dismukes, *Chem. Rev.* 97, 1 (1997).

22 S. Mukhopadhyay, S. K. Mandel, S. Bhaduri, W. H. Armstrong, *Chem. Rev.* 104, 3981 (2004).
23 R. Tagore, H. Chen, H. Zhang, R. N. Crabtree, G. W. Brudvig, *Inorg. Chim. Acta* 360, 2983 (2007).
24 M. Yagi, M. Toda, S. Yamada, H. Yamazaki, *Chem. Commun.* (2010) DOI: 10.1039/C0CC03114C.
25 R. Brimblecombe, A. Koo, G. C. Dismukes, G. F. Swiegers, L. Spiccia, *J. Am. Chem. Soc.* 132, 2892 (2010).
26 R. Bagai, G. Christou, *Chem. Soc. Rev.* 38, 1011 (2009).
27 J. Means et al., *J. Magn. Magn. Mater.* 284, 215 (2004).
28 J. Limburg, G. W. Brudvig, R. H. Crabtree, *J. Am. Chem. Soc.* 119, 2761 (1997).
29 C. W. Cady, K, E. Shinopoulos, R. H. Crabtree, G. W. Brudvig *Dalton Trans.* 39, 3985 (2010).
30 M. M. de Souza Sierra, K. Arend, A. N. Fernandes, M. Giovanela, B. Szpoganicz *Anal. Chim. Acta* 445, 89 (2001).

Example 2

The following are exemplar structures that can be modified into embodiments of the present disclosure by substituting ligands for a ligand(s) such as a carboxylate ligand (FIGS. 2.1 to 2.6).

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

At least the following is claimed:

1. A composition, comprising a polynuclear manganese cluster compound having oxygen-containing ligand, wherein the polynuclear manganese cluster compound has the formula $Mn_xM_yR_z$, wherein R is an oxygen containing ligand, M is Ca or Sr, x is 2 to 84, y is 0 to 2, and z is 8 to 24, wherein each oxygen-containing ligand is independently selected from the group consisting of: an alcohol group, an alkoxide group, an ether group, and a combination thereof.

2. The composition of claim 1, wherein the compound is dissolved in an aqueous solution.

3. The composition of claim 1, wherein the polynuclear manganese cluster compound includes 2, 3, 4, 6, 8, 12, 13, and 14, to 84 manganese atoms.

4. The composition of claim 1, wherein the oxygen-containing ligand is the alcohol group, wherein the alcohol group is represented by X(X')(X'')—C—OH, wherein X, X', and X'' are independently selected from the group consisting of: a substituted or unsubstituted alkyl group, a substituted or unsubstituted aryl group, and a substituted or unsubstituted heteroaryl group.

5. The composition of claim 1, wherein the oxygen-containing ligand is the alkoxide group, wherein the alkoxide group is represented by X(X')(X'')—C—O⁻, wherein X, X', and X'' are independently selected from the group consisting of: a substituted or unsubstituted alkyl group, a substituted or unsubstituted aryl group, and a substituted or unsubstituted heteroaryl group.

6. The composition of claim 1, wherein the oxygen-containing ligand is the ether group, wherein the ether group is represented by $(X—O—X')_n$, wherein n can be greater than 1 or 1 to 1000, wherein X and X' are independently selected from the group consisting of: a substituted or unsubstituted alkyl group, a substituted or unsubstituted aryl group, and a substituted or unsubstituted heteroaryl group.

7. The composition of claim 1, wherein the M is Ca or Sr and y is be 1 to 2.

8. The composition of claim 1, wherein the polynuclear manganese cluster further comprises ($H_2O$) groups.

\* \* \* \* \*